(12) United States Patent
Moos et al.

(10) Patent No.: US 6,319,429 B1
(45) Date of Patent: Nov. 20, 2001

(54) OXYGEN SENSITIVE RESISTANCE MATERIAL

(75) Inventors: Ralf Moos, Friedrichshafen; Wolfgang Menesklou, Rülzheim; Hans-Jürgen Schreiner, Schwegenheim; Karl Heinz Härdtl, Hagenbach, all of (DE)

(73) Assignee: DaimlerChrysler AG, Stuttgart-Mohringen (DE)

(*) Notice: Subject to any disclaimer, the term of this patent is extended or adjusted under 35 U.S.C. 154(b) by 0 days.

(21) Appl. No.: 09/543,487

(22) Filed: Apr. 6, 2000

Related U.S. Application Data

(63) Continuation-in-part of application No. PCT/DE98/02937, filed on Oct. 5, 1998.

(30) Foreign Application Priority Data

Oct. 8, 1997 (DE) .............................. 197 44 316

(51) Int. Cl.[7] .............................. H01B 1/08; G01N 27/00
(52) U.S. Cl. .............................. 252/519.15; 252/520.21; 252/521.1; 252/521.2; 436/137; 436/138; 423/21.1
(58) Field of Search .............................. 252/519.15, 520.21, 252/521.1, 521.2; 436/136, 137, 138; 439/913; 423/21.1, 138, 155; 427/126.3

(56) References Cited

U.S. PATENT DOCUMENTS

| 5,604,048 | * | 2/1997 | Nishihara et al. ............ 429/44 |
| 6,129,862 | * | 10/2000 | Munakata et al. ............ 252/519.15 |

FOREIGN PATENT DOCUMENTS

| 19839382-A1 | * | 3/1999 | (DE) . |
| 01240845-A2 | * | 9/1989 | (JP) . |

OTHER PUBLICATIONS

Moos et al (Materials for temperature independent resistive sensors . . . ), Sens. Actuators, B(2000), B67(1–2), 178–183 (Abstract Only), 2000.*

* cited by examiner

*Primary Examiner*—Mark Kopec
(74) *Attorney, Agent, or Firm*—Venable; Norman N. Kunitz

(57) ABSTRACT

Oxygen sensitive resistance materials for use with oxygen sensors, in particular λ probes are described. These materials are based on the fact that with complex metal oxides it is possible—by adding suitable doping substances—to achieve a negligible temperature dependence of the electric resistance of these materials for different oxygen partial pressures and to preset it to a desired partial pressure value.

44 Claims, 2 Drawing Sheets

ABSTRACT## OXYGEN SENSITIVE RESISTANCE MATERIAL

CROSS REFERENCE TO RELATED APPLICATION

This is a continuation-in-part application, filed under 35 U.S.C. §120, of PCT Application Ser. No. PCT/DE98/02937, filed Oct. 5, 1998 (designating the United States), which claims priority on German Patent Application DE 197 44 316.8-52, filed Oct. 8, 1997.

BACKGROUND OF THE INVENTION

1. Technical Field

The invention concerns a temperature independent oxygen sensitive resistance material on a titanate basis.

2. Description of the Related Art

Ever stricter exhaust gas limit values, in combination with the pressure to reduce fuel consumption, force automotive manufacturers to develop new concepts for combustion engines. It becomes clear that the above-mentioned requirements are best brought together when operating with excess air (air ratio $\lambda>1$). Such modern "lean concepts" require exact information on the oxygen content found in the exhaust gas. The principle of the standard potentiometric $\lambda$ probe can be designed with difficulty and some great effort only for high oxygen concentrations as they occur in such lean exhaust gases.

In order to be able to measure the oxygen content of the exhaust gas even within the lean area, it was proposed, for example, in EP 0 191 627, in DE 38 41 611, as well as in [1] to set up amperometric probes in accordance with the current limit principle ("Limit current probe") from a material containing oxygen ions.

Such a limit current sensor is, for instance, also contained in Chemical Abstract 191612 for JP 02269948, such that a fixed electrolytic body fitted with two electrodes located opposite each other is introduced, where one of the electrodes consists of a Perovskite type oxide with the general formula $L_{(1-x)}A_{(x)}Co_{(1-y)}M_{(y)}O_{(3-delta)}$, with A being Sr, Ba, Ca and L being La, Ce, Pr, Nd, but where no generic type $(Ti_{1-z}Fe_z)$ complex can arise, as for M only Fe, but not Ti and definitely no mixture of the two can be taken, which, however, according to the state of the art described below, would be fundamental for achieving a temperature independence from the working point of the oxygen partial pressure.

In addition, the operating mode of this sensor differs completely from resistive sensors and is based on an ion diffusion capability of an electrically insulating, but porous and for oxygen ions diffusion-capable layer, which is limited by a further gas-diffusion-controlling layer such that for an appropriate pump voltage a depletion in oxygen ions occurs, and the current flow to be measured now becomes dependent on the oxygen partial pressure. Any possibly occurring change in the ohmic resistance of a material of one of the electrodes will thus not be considered or utilized, and is rather regarded as an interfering factor.

However, according to DE 2334044 as well as pursuant to [2] there is also the option to utilize the oxygen partial pressure dependence of the electric conductivity of a metal oxidic material as a sensor effect, and to produce a sensor from this material, on the basis of whose electric resistance R it is possible to draw conclusions as to the oxygen partial pressure $PO^2$ of the exhaust gas, and, on that basis again, as to the oxygen content in the exhaust gas.

Doped titanium oxide ($TiO_2$) and strontium titanate ($SrTiO_3$) were investigated with particular thoroughness (DE 37 23 051.

EP 0 365 567, [2]), as—due to their chemical stability—such titanium oxides are capable of withstanding the extreme operating conditions within the exhaust gas train of a combustion engine.

However, sensors made up of these compounds—as of most other metal oxides—feature a very significant temperature dependence of the electrical resistance, which requires an extensive heating control system, in combination with major construction measures that will reduce the influence and effects of sudden changes in temperature.

Therefore, it was considered in DE 42 02 146, DE 42 44 723, DE 43 25 183 and EP 0 553 452 to use doped or undoped cuprates in future such as e.g. $La_2CuO_{4+y}$, as their electrical conductivity—specifically in the area of high oxygen content values, that is for $\mu>1$,—is temperature independent. For applications within the exhaust gas train, however, cuprates are not suitable, as they are chemically not all that stable and decompose at high temperatures and/or low oxygen partial pressures, such as e.g. during short term operation with a "rich" mixture ($\lambda<1$).

Lanthanferrites doped with alkaline earth, known from DE 44 18 054, feature a significantly higher chemical stability than cuprates. Their electrical conductivity also features a lower temperature dependence within the lean exhaust gas range ($\lambda>1$) when compared to $SrTiO_3$. However, sensors made from these materials show a greater temperature dependence of the electrical resistance value than sensors on a cuprate basis.

In EP 0 062 994 or in U.S. Pat. No. 4,454,494 with the same priority, Williams et al. proposed to replace the titanium (Ti) in $SrTiO_3$ in part by iron (Fe), and found out that sensors made from the compound $SrTi_{0.7}Fe_{0.3}O_{3-\delta}$ in lean atmospheres above 500° C.–600° C. have almost no temperature dependence of the electrical resistance but show a dependency on partial oxygen pressure according to $R \sim pO_2^{-1/5}$. Own measurements confirmed this but also showed that the temperature independence of the electric resistance will exist only at a partial oxygen pressure around $10^{-2}$ bar ($\lambda \approx 1.055$).

SUMMARY OF THE INVENTION

The present invention states oxygen sensitive resistance materials based on complex metal oxides where the disappearing temperature dependence of the electrical resistance of the sensor can be adjusted by adding suitable doping substances with regard to the oxygen partial pressure.

The material composition according to the invention has the advantage that the range for a complete temperature independence, that is, TKR=0, where TKR states the temperature coefficient of the electrical resistance of the sensor at a constant oxygen partial pressure of $$TKR = \frac{1}{R} \times \frac{\Delta R}{\Delta T}\bigg|pO_2 = const.$$

can be specifically shifted—by adding suitable doping materials—toward high as well as low oxygen partial pressure values. Due to this material composition it is possible to design the sensor such that the sensor signal of the sensor made therefrom will be independent of the actual temperature for specific engine concepts, which are characterized by a specific oxygen content in the exhaust gas. In respect of any such sensor, there is no need for a complex and costly heating control system, which produces a major cost advantage when compared to known principles. In addition, the sensor can be designed such, by adding further doping materials in accordance with the invention, that the temperature coefficient of its electrical resistance will still remain negligble even in the event of greater deviations from the above-mentioned working point.

DETAILED DESCRIPTION OF THE INVENTION

Using a material composition in accordance with the invention, the temperature independence range of the electric sensor resistance can be shifted into the range of $\lambda>2$, that is $PO_2>0.1$ bar, which is the relevant range for Diesel engines and "lean Otto engines". This can be seen quite clearly from FIG. 1. There, the resistance of a sensor, built up from a material composition in accordance with the invention, is plotted against the oxygen partial pressure of the exhaust gas. Here, in the original compound $SrTi_{1-z}Fe_zO_{3-\delta}$ one part of the strontium, which occurs as a bivalent, was replaced by a trivalent ion of class M, which embeds itself in a strontium position. This material composition, in the following designated as material class 1a, thus is: p1 $Sr_{1-a}M_aTi_{1-z}Fe_zO_{3-\delta}$.

Figure 1:
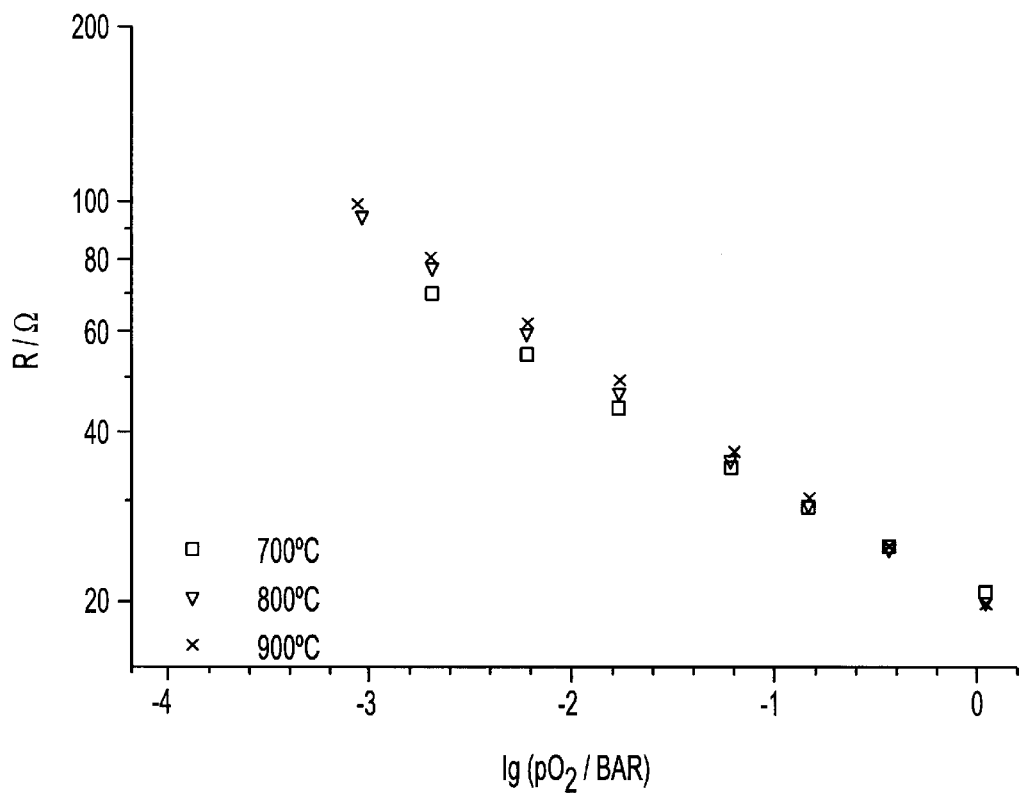
FIG. 1 shows the resistance R of a sensor, built up from a material of material category 1a ($Sr_{1-a}M_aTi_{1-z}Fe_zO_{3-\delta}$), here as an example with z=0.3, M=Lanthan (La), and a=0.05) applied in a double logarithm against the oxygen partial pressure $PO_2$ of the exhaust gas. The parameter is the temperature T of the sensor.

By way of example, M=Lanthan (La), a=0.05 and in accordance with EP 0 062 994 z=0.3 were selected in FIG. 1. The same effect will also be achieved by replacing strontium with quadrivalent ions M, which embed themselves in a strontium position. Also, replacing titanium and iron by pentavalent or hexavalent ions M' in accordance with $Sr(Ti_{1-z}Fe_z)_{1-b}M'_bO_{3-\delta}$ (material class 1b) will lead to the same result. In FIG. 1, it can be clearly seen how the temperature independence range of the sensor resistance value has shifted to higher oxygen partial pressures in comparison with EP 0 062 994; here, for example, to $pO_2\approx 0.1$ bar, that is $\lambda\approx 2$).

The complete or partial replacement of the bivalent strontium by means of another bivalent element N, e.g. $N_{1-a}M_aTi_{1-z}Fe_zO_{3-\delta}$ or $(Sr_{1-n}N_n)_{1-a}M_aTi_{1-z}Fe_zO_{3-\delta}$, or $N(Ti_{1-z}Fe_z)_{1-b}M'_bO_{3-\delta}$ or $(Sr_{1-n}N_n)(Ti_{1-z}Fe_z)_{1-b}M'_bO_{3-\delta}$, is to be regarded as being included in material class 1.

Typical examples for N are Barium (Ba) or Calcium (Ca). Here, n may assume values from zero (strontium is not replaced) to one (strontium is fully replaced), without there being a fundamental change in the sensor characteristics. $\delta$ characterizes the oxygen deficit which occurs, depending on the composition, due to the electron neutrality condition.

Also included in material class 1 are materials in accordance with the above-mentioned composition, in which the quadrivalent titanium is replaced fully or partially by one or several quadrivalent elements. Here, too, sensor characteristics change insignificantly only. Typical examples for such quadrivalent elements are zirconium (Zr) and tin (Sn). The titanium may also be fully or partially replaced with tin (Sn), silicon (Si), germanium (Ge), cerium (Ce), and hafnium (Hf).

Figure 2:
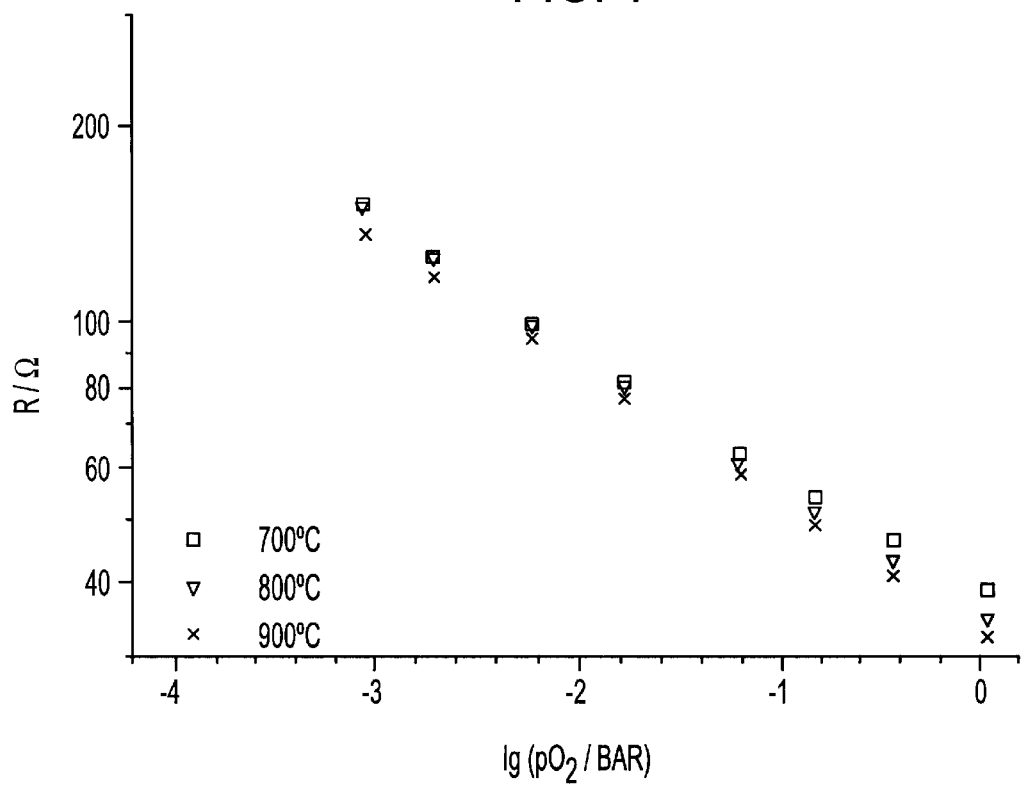
FIG. 2 shows the resistance R of a sensor, built up from a material of material category 2a ($Sr(Ti_{1-z}Fe_z)_{1-c}M''_cO_{3-\delta}$), here as an example with z=0.3, M''=Gallium (Ga) and c=0.05) applied in a double logarithm against the oxygen partial pressure $PO_2$ of the exhaust gas. The parameter is the temperature T of the sensor.

FIG. 2 shows how the temperature independent range of the sensor resistance shifts to lower oxygen partial pressures and thus to a lower exhaust gas oxygen content due to the partial replacement of titanium or iron by a trivalent or bivalent ion M'' in accordance with $Sr(Ti_{1-z}Fe_z)_{1-c}M''_cO_{3-\delta}$ (material class 2a). By way of example, this is shown here by z=0.3, M''=Gallium (Ga) and c=0.05. The same effect is achieved by replacing the strontium with a monovalent ion M'''. The composition will then be $Sr_{1-d}M'''_dTi_{1-z}Fe_zO_{3-\delta}$ (material class 2b) .Using material classes 1 and 2, a material system will thus be available which, depending on its composition, will provide for the manufacture of a resistive oxygen sensor, whose sensor resistance features a disappearing temperature dependence range that can be shifted towards any desired oxygen partial pressures. The same applies to replacing strontium by a bivalent ion, or replacing the titanium by a quadrivalent ion.

Figure 3:
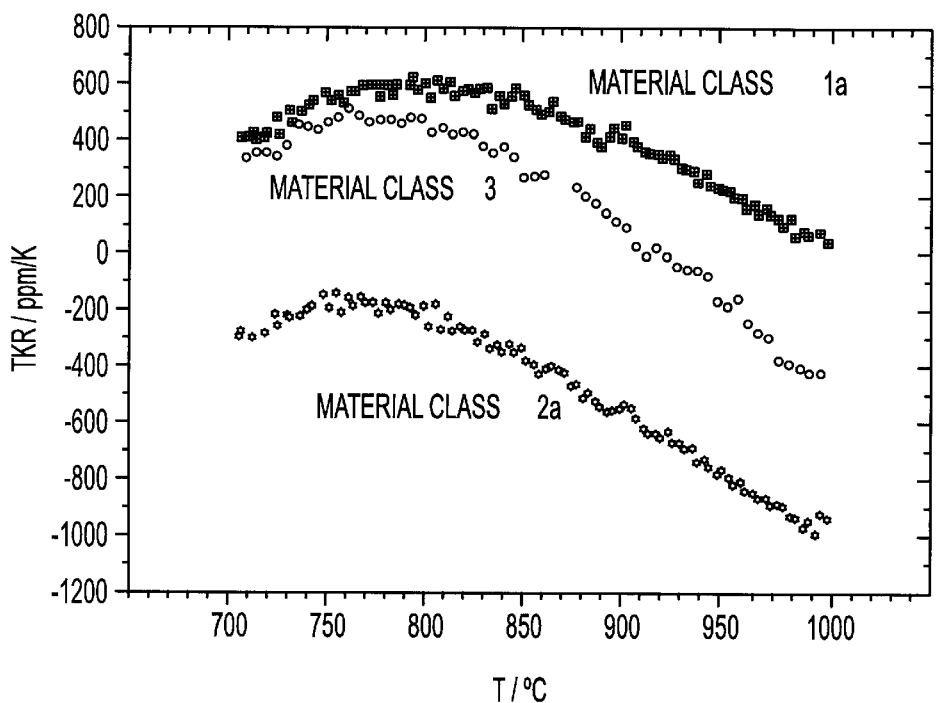
FIG. 3 shows the comparison of the temperature coefficient of the resistance TKR for three sensors, built up from materials of the material classes 1a, 2a, and 3, where material class 3 represents a mixture made up of material classes 1 and 2. By way of example, a mixture ratio of 1:1 from material classes 1a and 2a was selected here, with z=0.3, M=Lanthan (La), a=0.05, M''=Gallium (Ga), and c=0.05.

In FIG. 2 it is to be noted that in the range, within which the sensor resistance still features a temperature dependence, its TKR is <0, whilst the sensor characteristic from FIG. 1 in the range that is not temperature independent has a TKR>0. From a combination of two sensors built up from material classes 1 and 2, which are electrically connected in a suitable fashion, it is thus possible to produce a sensor which, across the entire exhaust gas range occurring for lean combustion engines, has a still lower or—if a suitable composition is selected—disappearing temperature dependence. But such a combination may also be any given combination of material classes 1 and 2 to a material class 3, from which the sensor will then be built up. Such an example is shown in FIG. 3. Due to a particularly suitable combination of material classes 1a and 2a, and here in the ratio 1:1, the temperature coefficient of the sensor resistance—across the entire temperature range—will be of a smaller amount than for any material class 1a or 2a on an individual basis. A major variation of the temperature coefficient of the sensor resistance and its temperature independent oxygen partial pressure range can be achieved by a suitable combination of the parameters a and/or b, c and/or d and the mixture ratio.

Figure 4:
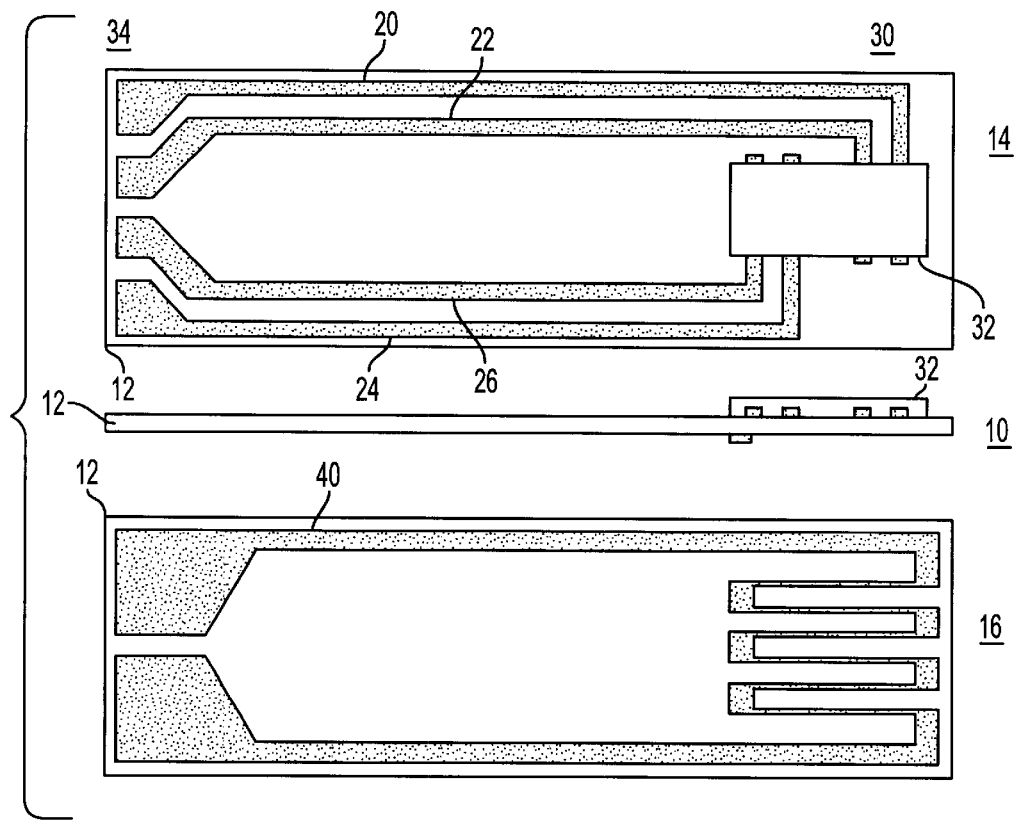
FIG. 4 shows an embodiment in thick film technology.

FIG. 4 shows a possible very simple embodiment 10 in thick film technology. On the top surface 14 of a substrate 12 there are four electrical connection tracks 20, 22, 24, 26. At one end 30, the connection tracks are covered, as drawn, by a gas sensitive film 32 consisting of material classes 1 or 2 or 3. At the opposite end, terminal 34 is provided with contact surfaces for attaching electric supply lines. In this way, the film resistance can be measured in four-wire technology. Then the contact resistance between electrode and film material will no longer play any part. On the underside 16 of substrate 12 a heater track 40 is applied, which heats the gas sensitive film to the temperature range shown in FIGS. 1 to 3. A precise temperature control system is not required in the case of the material compositions in accordance with the invention. An associated sensor housing is not shown here.

Below, in an example, the production of a powder in accordance with the invention for material class 1a) is described. $SrCO_3$, $M_2O_3$, $TiO_2$, and $Fe_2O_3$ will be weighed in such that the desired stoichiometry ratio is achieved. For z=0.3, a=0.05, and M=La, a mass ratio of $SrCO_3$, $La_2O_3$, TiO2, and $Fe_2O_3$, as calculated from the molar masses, must be weighed in such that the atomic ratio Sr:La:Ti:Fe is 19:1:14:6. As $La_2O_3$ is hygroscopic, it is first annealed at approx. 850° C. and then weighed in when hot. A typical preparation of approx. 50 g raw powder will then be filled into a grinding cup together with a grinding medium, for which e.g. a solvent such as e.g. cyclohexane or isopropanol is used; grinding balls, made of agate for instance, diameter 10 mm for a quantity of 50 pcs. or a lower ball diameter for a correspondingly greater quantity of grinding balls, are added; the entire preparation will then be mixed in a planetary ball mill for a period of one to four hours. The grinding material mixed in this way will then be dried, separated from the grinding balls, filled into a crucible, and fired for 15 hours in a furnace in air atmosphere at 1200° C. The cooled down powder will then have the desired material composition which is shown e.g. by x-ray diffractometer analysis. A powder fired in this way must still be crushed by means of a further grinding stage, in order to achieve a powder grain size distribution suitable for the further sensor production process. A typical grinding process is executed as described above, but to this end 7–10 balls with 20 mm diameter each are used. Also, powder crushing is effected in an attritor mill or an annular clearance ball mill. The dried powder, separated from the grinding balls, will then be used for sensor production.

The powders of material classes 1b, 2a, 2b, and 3 are also produced in analogy to the process described. Depending on the composition, it will then be possible to replace $M_2O_3$ with the corresponding oxides, carbonates, or oxycarbonates as base material. These will then be weighed in according to the then valid stoichiometry.

From the original materials made in accordance with example 1, sensors are produced as follows. The powders will be brought into a suitable form; if necessary, a suitable binding agent can be used for this purpose, pressed, and sintered in air at temperatures between 1300° C. and 1400° C. The typical dimensions of a sinter body are 25 mm×3 mm×0.2 mm. This sensor body will then be contacted with platin wires, which are fixed with a platin firing paste. The paste can be fired at e.g. 1050° C. Two, three, or four such platin electrodes will be applied. Correspondingly, the resistance measurement will then be effected by means of two wire, three wire or four wire measurement. A single heater, consisting of a heater wire and an electrical insulation, which is necessary to separate sensor and heater from one another, still needs to be fitted, in order to compensate an exhaust gas temperature which is too low, and to bring the sensor up to operating temperature as early as possible. Finally, the sensor is introduced into a suitable protective housing.

Alternatively, a sensor in accordance with the invention can be built up in thick film technology. The powders made from the original materials produced in accordance with the above-mentioned process are mixed with suitable media which render the original material capable of screen printing. On a substrate made of e.g. $Al_2O_3$ or $ZrO_2$, appropriate connection tracks, made of gold or platin, are printed in screen printing technology, in order to be able to measure the sensor resistance in a two wire, three wire, or four wire arrangement. These tracks are typically burnt in in an air atmosphere. Then the sensor film will be printed and also burnt in. On the back of the sensor, a further heating film will be applied which features the above-described functions. Supply lines are connected to the electrodes of the measurement tracks and heater tracks. Setup takes place in accordance with FIG. 4. A suitable housing provided with electrical feedthroughs ensures mechanical stability and protects the sensor.

The above-described oxygen sensitive resistance materials are suitable for a multitude of applications. Thus there is a provision for using oxygen sensors to determine the oxygen content in fuel/air mixtures, in the exhaust gas of combustion engines, in plants for the removal of nitrogen or desulphurization plants, in sinter furnaces, in bioreactors, and in facilities, which due to combustion—especially of carbon-, hydrocarbon- or hydrogen-rich fuels—produce thermal energy as usable energy. Here, a respective adaptation of the resistance material to the respective existing oxygen partial pressure is provided, in order to ensure to a large extent that temperature independence is achieved in this working point.

LITERATURE

[1] Kleitz M., Siebert E., Fabry P., Fouletier J.: Solid-State Electrochemical Sensors.
   In: Sensors. A comprehensive Survey. Chemical and Biochemical Sensors Part I. Göpel W. et al. (Publ.), VCH-Verlag, Weinheim, 1991, Page 341–428.
[2] Schönauer U.: "Dickschicht Sauerstoffsensoren auf der Basis keramischer Halbleiter." (Thick film oxygen sensors based on ceramic semiconductors). Technisches Messen 56[6] 260–263, 1989.

What is claimed is:

1. An oxygen sensor comprising a material composition, comprising one or more complex metal oxides selected from the group consisting of material classes 1a) represented by general structure $(Sr_{1-n}N_n)_{1-a}M_aTi_xX_yFe_zO_{3-\delta}$ 1b) represented by general structure $(Sr_{1-n}N_n)(Ti_xX_yFe_z)_{1-b}M'_bO_{3-\delta}$ 2a) represented by general structure $(Sr_{1-n}N_n)(Ti_xX_yFe_z)_{1-c}M''_cO_{3-\delta}$ and 2b) represented by general structure $(Sr_{1-n}N_n)_{1-a}M'''_aTi_xX_yFe_zO_{3-\delta}$ wherein:

Sr is strontium, Ti is titanium, Fe is iron;

O is oxygen;

N is a bivalent element or elements selected from the group consisting of barium, calcium, magnesium, zinc, cadmium, mercury, lead, and mixtures thereof;

X is a tetravalent element selected from the group consisting of silicon, germanium, zirconium, tin, cerium, and hafnium;

M is a trivalent or tetravalent element or elements selected from the group consisting of a lanthanide element, a mixture of lanthanide elements, yttrium, indium, thallium, and mixtures thereof;

M' is a pentavalent or hexavatent element or elements selected from the group consisting of phosphorus, vanadium, arsenic, niobium, antimony, tantalum, molybdenum, tungsten, and mixtures thereof;

M" is a bivalent or trivalent element or elements selected from the group consisting of aluminum, scandium, gallium, chromium, manganese, cobalt, nickel, and mixtures thereof;

M''' is a monovalent element or elements selected from the group consisting of lithium, sodium, potassium, rubidium, cesium, copper, silver, and mixtures thereof;

n is greater than or equal to zero, and less than or equal to 1;

a, b, c, and d are independently greater than zero and less than or equal to 0.5;

the sum of x+y+z is 1, wherein z is from 0.1 to 0.6, x is from zero to 0.9, and y is from zero to 0.9; and δ is the oxygen deficit which is to be applied according to the composition in order to establish electrical neutrality of the complex metal oxides.

2. An oxygen sensor according to claim 1, wherein

N is an element selected from the group consisting of barium, calcium, and mixtures thereof.

3. An oxygen sensor according to claim 1, wherein the material composition comprises material class 1a, of general structure

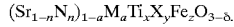

$(Sr_{1-n}N_n)_{1-a}M_aTi_xX_yFe_zO_{3-\delta}.$

4. A sensor according to claim 1, wherein the material composition comprises material class 1b, of general structure

$(Sr_{1-n}N_n)(Ti_xX_yFe_z)_{1-b}M'_bO_{3-\delta}.$

5. A sensor according to claim 1, wherein the material composition comprises material class 2a, of general structure

$(Sr_{1-n}N_n)(Ti_xX_yFe_z)_{1-c}M''_cO_{3-\delta}.$

6. An oxygen sensor according to claim 1, wherein the material composition comprises compounds of the group 2b, of general structure

$(Sr_{1-n}N_n)(Ti_xX_yFe_z)_{1-b}M'_bO_{3-\delta}.$

7. An oxygen sensor according to claim 1, wherein the material composition comprises a mixture of components from at least two of the material classes 1a, 1b, 2a, or 2b.

8. An oxygen sensor according to claim 1 comprsing a first component and a second component, wherein the first component is selected from the group consisting of compounds of material class 1a, compounds of material class 1b, and mixtures thereof; and the second component is selected from the group consisting of compounds of material class 2a, compounds of material class 2b, and mixtures thereof.

9. An oxygen sensor according to claim 1, wherein y is zero.

10. An oxygen sensor according to claim 1, wherein y is less than x;

z is greater than or equal to 0.2, and less than or equal to 0.45;

a, b, c, and d are greater than 0 and less than or equal to z; and n is greater than or equal to zero and less than or equal to 1.

11. An oxygen sensor according to claim 1, wherein y is less than 0.25x; and a, b, ca and d are independently less than or equal to 0.1.

12. An oxygen sensor according to claim 1, wherein y is less than 0.25x, and wherein the material composition comprises at least one component from material class 1a, of general structure

$(Sr_{1-n}N_n)_{1-a}M_aTi_xX_yFe_zO_{3-\delta}$ wherein z is greater than or equal to 0.2 and less than or equal to 0.45;

a is greater than 0 and less than 0.1;

n is greater than or equal to 0 and less than or equal to 1;

M is lanthanum (La) or yttrium (Y) and

N is selected from the group consisting of barium, calcium, magnesium, cadmium, lead, and mixtures thereof.

13. An oxygen sensor according to claim 1, wherein y is less than 0.25x, and wherein the material composition comprises at least one component from material class 1b, of general structure

$(Sr_{1-n}N_n)(Ti_xX_yFe_z)_{1-b}M'_bO_{3-\delta}$ wherein;

z is greater than or equal to 0.2 and less than or equal to 0.45;

b is greater than 0 and less than or equal to 0.1;

n is greater than or equal to 0 and less than or equal to 1,

M' is niobium, antimony, or tantalum; and

N is selected from the group consisting of barium, calcium, magnesium, cadmium, lead, and mixtures thereof.

14. An oxygen sensor according to claim 1, wherein y is less than 0.25x, and wherein the material composition comprises at least one component from material class 2a, of general structure

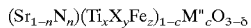

$(Sr_{1-n}N_n)(Ti_xX_yFe_z)_{1-c}M''_cO_{3-\delta}$ wherein;

z is greater than or equal to 0.2 and less than or equal to 0.45;

c is greater than 0 and less than or equal to 0.1;

n is greater than or equal to 0 and less than or equal to 1; and

M'' is gallium or aluminum; and

N is selected from the group consisting of barium, calcium, magnesium, cadmium, lead, and mixtures thereof.

15. An oxygen sensor according to claim 1, wherein y is less than 0.25x, and wherein the material composition comprises at least one component from material class 2b, of general structure

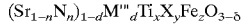

$(Sr_{1-n}N_n)_{1-d}M'''_dTi_xX_yFe_zO_{3-\delta}$ wherein:

z is greater than or equal to 0.2 and less than or equal to 0.45;

c is greater than 0 and less than or equal to 0.1; and n is greater than or equal to 0 and less than or equal to 1; and N is selected from the group consisting of bariumn, calcium, magnesium, cadmium, lead, and mixtures thereof.

16. An oxygen sensor according to claim 1, wherein the material composition comprises a first component and a second component wherein the first component is selected from the group consisting of compounds of material class 1a, compounds of material class 1b, and mixtures thereof; and the second component is selected from the group consisting of compounds of material class 2a, compounds of material class 2b, and mixtures thereof;

wherein
y is less than 0.25x
z is greater than or equal to 0.2 and less than or equal to 0.45;
a and c are independently greater than 0 and less than or equal to 0.1;
n is greater than or equal to 0 and less than or equal to 1;
M is lanthanum or yttrium;
M" is gallium or aluminum; and
N is selected from the group consisting of barium, calcium, magnesium, cadmium, lead, and mixtures thereof.

17. An oxygen sensor according to claim 1, wherein y is less than 0,25x and wherein the material composition comprises
a component of group 1a, of general structure $(Sr_{1-n}N_n)_{1-a}M_aTi_xX_yFe_zO_{3-\delta}$ and a component of group 2a, of general structure $(Sr_{1-n}N_n)(Ti_xX_yFe_z)_{1-c}M''_cO_{3-\delta}$ wherein:
z is greater than or equal to 0.2 and less than or equal to 0.45;
a and c are independently greater than 0 and less than or equal to 0.1;
n is greater than or equal to 0 and less than or equal to 1;
M is lanthanum or yttrium;
M" is gallium or aluminum; and
N is selected from the group consisting of barium, calcium, magnesium, cadmium, lead, and mixtures thereof.

18. An oxygen sensor according to claim 17, wherein
M is lanthanum;
M" is gallium; and
N is an element or elements selected from the group consisting of barium, calcium, magnesium and mixtures thereof.

19. An oxygen sensor according to claim 18, wherein the resulting temperature coefficient of the electrical resistance is zero.

20. An oxygen sensor according to claim 1, comprising a sintered body to which electrodes are applied.

21. An oxygen sensor according to claim 1, further comprising an electrical connection,
wherein the material cornposition comprises at least two materials selected from different material classes,
wherein one of the selected materials features a negative temperature coefficient of the electrical resistance and the other a positive temperature coefficient of the electrical resistance, with both material classes and the type of electrical connection being selected such that the resulting temperature coefficient of the electrical resistance becomes smaller than the individual temperature coefficients of the selected materials.

22. A method for manufacturing an oxygen sensor of claim 1, comprising
weighing the oxides, carbonates, and/or oxycarbonates of the metals occurring in the material composition in molar amounts corresponding to the stoichiometric ratio of the metals in the material composition;
finely mixing the oxides, carbonates, and/or oxycarbonates;
grinding in an organic solvent;
drying and firing the oxides, carbonates, and/or oxycarbonates to form a metal oxide powder;
working the oxide powder into a paste;
applying the paste to and burning the paste onto a substrate that is electrically insulating; and
applying electrodes,
wherein the electrodes are applied either before or after burning in the metal oxide paste.

23. A material composition, suitable for use in an oxygen sensor, comprising one or more complex metal oxides selected from the group consisting of material classes
1a) represented by general structure $(Sr_{1-n}N_n)_{1-a}M_aTi_xX_yFe_zO_{3-\delta}$
1b) represented by general structure $(Sr_{1-n}N_n)(Ti_xX_yFe_z)_{1-b}M'_bO_{3-\delta}$
2a) represented by general structure $(Sr_{1-n}N_n)(Ti_xX_yFe_z)_{1-c}M''_cO_{3-\delta}$ and
2b) represented by general structure $(Sr_{1-n}N_n)_{1-d}M'''_dTi_xX_yFe_zO_{3-\delta}$
wherein:
Sr is strontium, Ti is titanium, Fe is iron;
O is oxygen;
N is a bivalent element or elements selected from the group consisting of barium, calcium, magnesium, zinc, cadmium, mercury, lead, and mixtures thereof;
X is a tetravalent element selected from the group consisting of silicon, germanium, zirconium, tin, cerium, and hafnium;
M is a trivalent or tetravalent element or elements selected from the group consisting of a lanthanide element, a mixture of lanthanide elements, yttrium, indium, thallium, and mixtures thereof;
M' is a pentavalent or hexavalent element or elements selected from the group consisting of phosphorus, vanadium, arsenic, niobium, antimony, tantalum, molybdenum, tungsten, and mixtures thereof;
M" is a bivalent or trivalent element or elements selected from the group consisting of aluminum, scandium, gallium, chromium, manganese, cobalt, nickel, and mixtures thereof;
M''' is a monovalent element or elements selected from the group consisting of lithium, sodium, potassium, rubidium, cesium, copper, silver, and mixtures thereof;
n is greater than or equal to zero, and less than or equal to 1;
a, b, c, and d are independently greater than zero and less than or equal to 0.5;
the sum of x+y+z is 1, wherein z is from 0.1 to 0.6, x is from zero to 0.9, and y is from zero to 0.9; and
δ is the oxygen deficit which is to be applied according to the composition in order to establish electrical neutrality of the complex metal oxides.

24. A composition according to claim 23, wherein
N is an element selected from the group consisting of barium, calcium, and mixtures thereof.

25. A composition according to claim 23, comprising material class 1a, of general structure $(Sr_{1-n}N_n)_{1-a}M_aTi_xX_yFe_zO_{3-\delta}$ 26. A composition according to claim 23, comprising material class 1b, of general structure $(Sr_{1-n}N_n)(Ti_xX_yFe_z)_{1-b}M'_bO_{3-\delta}$ 27. A composition according to claim 23, comprising material class 2a, of general structure

28. A composition according to claim 23, wherein the material composition comprising material class 2b, of general structure

29. A composition according to claim 23, comprising a mixture of components from at least two of the material classes 1a, 1b, 2a, or 2b.

30. A composition according to claim 23 comprising a first component and a second component, wherein
    the first component is selected from the group consisting of compounds of material class 1a, compounds of material class 1b, and mixtures thereof; and
    the second component is selected from the group consisting of compounds of material class 2a, compounds of material class 2b, and mixtures thereof.

31. A composition according to claim 23, wherein y is zero.

32. A composition according to claim 23, wherein
    y is less than x;
    z is greater than or equal to 0.2, and less than or equal to 0.45;
    a, b, c, and d are greater than 0 and less than or equal to z and
    n is greater than or equal to zero and less than or equal to 1.

33. A composition according to claim 23, wherein
    y is less than 0.25x; and
    a, b, c, and d are Independently less than or equal to 0.1.

34. A composition according to claim 23, comprising at least one component from material class 1a, of general structure

wherein:
    y is less than 0.25x;
    z is greater than or equal to 0.2 and less than or equal to 0.45;
    a is greater than 0 and less than 0.1;
    n is greater than or equal to 0 and less than or equal to 1;
    M is lanthanum (La) or yttrium (Y); and
    N is selected from the group consisting of barium, calcium, magnesium, cadmium, lead, and mixtures thereof.

35. A composition according to claim 23, comprising at least one component from material class 1b, of general structure

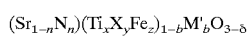

wherein:
    y is less than 0.25x;
    z is greater than or equal to 0.2 and less than or equal to 0.45;
    b is greater than 0 and less than or equal to 0.1;
    n is greater than or equal to 0 and less than or equal to 1;
    M' is niobium, antimony, or tantalum; and
    N is selected from the group consisting of barium, calcium, magnesium, cadmium, lead, and mixtures thereof.

36. A composition according to claim 23, comprising at least one component from material class 2a, of general structure

wherein:
    y is less than 0.25x;
    z is greater than or equal to 0.2 and less than or equal to 0.45;
    c is greater than 0 and less than or equal to 0.1;
    n is greater than or equal to 0 and less than or equal to 1; and
    M" is gallium or aluminum, and
    N is selected from the group consisting of barium, calcium, magnesium, cadmium, lead, and mixtures thereof.

37. A composition according to claim 23, comprising at least one component from material class 2b, of general structure

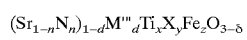

wherein:
    y is less than 0.25x;
    z is greater than or equal to 0.2 and less than or equal to 0.45;
    c is greater than 0 and less than or equal to 0.1; and
    n is greater than or equal to 0 and less than or equal to 1; and
    N is selected from the group consisting of barium, calcium, magnesium, cadmium, lead, and mixtures thereof.

38. A composition according to claim 23, comprising a first component and a second component, wherein
    the first component is selected from the group consisting of compounds of material class 1a, compounds of material class 1b, and mixtures thereof; and
    the second component is selected from the group consisting of compounds of material class 2a, compounds of material class 2b, and mixtures thereof;
    wherein;
    y is less than 0.25x;
    z is greater than or equal to 0.2 and less then or equal to 0.45;
    a and c are independently greater than 0 and less than or equal to 0.1;
    n is greater than or equal to 0 and less than or equal to 1:
    M is lanthanum or yttrium;
    M" is gallium or aluminum; and
    N is selected from the group consisting of barium, calcium, magnesium, cadmium, lead, and mixtures thereof.

39. A composition according to claim 23, comprising a component of group 1a, of general structure

and a component of group 2a, of general structure

wherein:

y is less than 0.25x.

z is greater than or equal to 0.2 and less then or equal to 0.45;

a and c are independently greater than 0 and less than or equal to 0.1;

n is greater than or equal to 0 and less than or equal to 1;

M is lanthanum or yttrium;

M" is gallium or aluminum; and

N is selected from the group consisting of barium, calcium, magnesium, cadmium, lead, and mixtures thereof.

40. A composition according to claim 39, wherein

M is lanthanum;

M" is gallium; and

N is an element or elements selected from the group consisting of barium, calcium, magnesium and mixtures thereof.

41. A method for designing an oxygen sensor based on complex metal oxides with the general formula

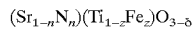

$(Sr_{1-n}N_n)(Ti_{1-z}Fe_z)O_{3-\delta}$ by changing the position of the working point of the sensor toward a higher oxygen potential, wherein Sr is strontium, Ti is titanium, Fe is iron;

N is a bivalent element selected from the group consisting of barium (Ba), calcium (Ca), magnesium (Mg), zinc (Zn), cadmium (Cd), mercury (Hg), lead (Pb) and mixtures thereof;

n is greater than zero and less than one;

z is greater than equal to 0.1 and less than or equal to 0.6; and

δ is the oxygen deficit, which, depending on the respective composition, occurs in accordance with the electron neutrality condition, the method comprising at least one of the steps of:

1) partially replacing the bivalent $(Sr_{1-n}N_n)$ by trivalent and/or tetravalent M where M is selected from the group consisting of a lanthanide element, yttrium, indium, thallium, and mixtures thereof; and 2) partially replacing quadrivalent $(Ti_{1-z}Fe_z)$ by pentavalent and/or hexavalent M', where M' is selected from the group consisting of phosphorus (P), vanadium (V), arsenic (As), niobium (Nb), antimony (Sb), tantalum (Ta), molybdenum (Mo), tungsten (W), and mixtures thereof.

42. An oxygen sensor designed according to the method of claim 41.

43. A method for designing an oxygen sensor based on complex metal oxides with the general formula

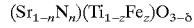

$(Sr_{1-n}N_n)(Ti_{1-z}Fe_z)O_{3-\delta}$ by changing the position of the working point of the sensor toward a lower oxygen potential, wherein Sr is strontium, Ti is titanium, Fe is iron;

N is a bivalent element selected from the group consisting of barium (Ba), calcium (Ca), magnesium (Mg), zinc (Zn), cadmium (Cd), mercury (Hg), lead (Pb), and mixtures thereof;

n is greater than zero and less than one;

z is greater than or equal to 0.1 and less than or equal to 0.6; and

δ is the oxygen deficit, which, depending on the respective composition, occurs in accordance with the electron neutrality condition, the method comprising at least one of the steps of 1) partially replacing tetravalent $(Ti_{1-z}Fe_z)$ by trivalent and/or bivalent M", where M" is selected from the group consisting of aluminum (Al), scandium (Sc), gallium (Ga), chromium (Cr), manganese (Mn), cobalt (Co), nickel (Ni), and mixtures thereof; and 2) partially replacing bivalent $(Sr_{1-n}N_n)$ by monovalent M''', where M''' is selected from the group consisting of lithium (Li), sodium (Na), potassium (K), rubidium (Rb), cesium (Cs), copper (Cu), silver (Ag), and mixtures thereof.

44. An oxygen sensor designed according to the method of claim 43.

\* \* \* \* \*